United States Patent
Kam et al.

(10) Patent No.: US 9,974,471 B1
(45) Date of Patent: May 22, 2018

(54) ANALYTE DETECTION SYSTEM AND METHOD FOR INTRADERMAL IMPLANTATION OF BIOCOMPATIBLE OPTODE NANOSENSORS

(71) Applicant: Verily Life Sciences LLC, Mountain View, CA (US)

(72) Inventors: Kimberly Kam, Mountain View, CA (US); Jerrod Joseph Schwartz, Mountain View, CA (US); Vasiliki Demas, Mountain View, CA (US); Vikram Singh Bajaj, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 115 days.

(21) Appl. No.: 14/580,768

(22) Filed: Dec. 23, 2014

Related U.S. Application Data

(60) Provisional application No. 62/068,194, filed on Oct. 24, 2014.

(51) Int. Cl.
*A61B 5/1455* (2006.01)
*A61B 5/145* (2006.01)
*A61B 5/00* (2006.01)

(52) U.S. Cl.
CPC ........ *A61B 5/14514* (2013.01); *A61B 5/0071* (2013.01); *A61B 5/1451* (2013.01); *A61B 5/1455* (2013.01); *A61B 5/14503* (2013.01)

(58) Field of Classification Search
CPC ... A61B 5/0059; A61B 5/1459; A61B 5/0071; A61B 5/14532; A61B 5/14551; G01N 21/6428
See application file for complete search history.

(56) References Cited

U.S. PATENT DOCUMENTS

| | | |
|---|---|---|
| 2,784,127 A | 3/1957 | Joyner et al. |
| 4,444,933 A | 4/1984 | Columbus et al. |
| (Continued) | | |

FOREIGN PATENT DOCUMENTS

| | | |
|---|---|---|
| WO | 00/74763 A2 | 12/2000 |
| WO | 2009/040548 A1 | 4/2009 |
| (Continued) | | |

OTHER PUBLICATIONS

Balaconis, et al., "Biodegradable Optode-based Nanosensors for In-Vivo Monitoring", Anal. Chem., Jul. 3, 2012, vol. 84(13), pp. 5787-5793, doi:10.1021/ac301137c.
(Continued)

*Primary Examiner* — Eric Winakur
*Assistant Examiner* — Chu Chuan (JJ) Liu
(74) *Attorney, Agent, or Firm* — McDonnell Boehnen Hulbert & Berghoff LLP

(57) ABSTRACT

A device and system for measuring and/or monitoring an analyte present on the skin is provided. The system includes a skin-mountable device that may be attached to an external skin surface and a reader device. The skin-mountable device includes a substrate, a plurality of micro-needles, and nanosensors. The micro-needles are attached to the substrate such that attachment of the substrate to an external skin surface causes to the micro-needles to penetrate into the epidermis, intradermis, or dermis. The nanosensors include a detectable label and are configured to interact with a target analyte present in the interstitial fluid in the epidermis, intradermis, or dermis. The reader device is configured to detect the analyte in interstitial fluid via interaction with the skin-mountable device.

24 Claims, 8 Drawing Sheets

(56) References Cited

U.S. PATENT DOCUMENTS

| | | | |
|---|---|---|---|
| 6,503,231 | B1 | 1/2003 | Prausnitz et al. |
| 7,344,499 | B1 | 3/2008 | Prausnitz et al. |
| 7,785,301 | B2 | 8/2010 | Yuzhakov |
| 8,263,358 | B2 | 9/2012 | Clark et al. |
| 8,470,300 | B2 | 6/2013 | Clark et al. |
| 8,708,966 | B2 | 4/2014 | Allen et al. |
| 8,765,458 | B2 | 7/2014 | Clark et al. |
| 2002/0138049 | A1 | 9/2002 | Allen et al. |
| 2007/0027507 | A1* | 2/2007 | Burdett ............... A61B 5/0002 607/60 |
| 2007/0191696 | A1* | 8/2007 | Mischler ............... A61B 5/157 600/310 |
| 2007/0276211 | A1* | 11/2007 | Mir ............... A61B 5/14532 600/345 |
| 2008/0125743 | A1* | 5/2008 | Yuzhakov ............... A61M 37/0015 604/506 |
| 2008/0213461 | A1* | 9/2008 | Gill ............... A61K 9/0021 427/2.3 |
| 2008/0275318 | A1 | 11/2008 | Lastovich et al. |
| 2009/0247984 | A1* | 10/2009 | Lamego ............... A61B 5/14532 604/506 |
| 2010/0069726 | A1* | 3/2010 | Levinson ............... A61B 5/14532 600/309 |
| 2010/0198034 | A1* | 8/2010 | Thomas ............... A61B 5/14532 600/365 |
| 2010/0312191 | A1* | 12/2010 | Allen ............... A61B 5/1411 604/173 |
| 2011/0160069 | A1* | 6/2011 | Corrie ............... A61B 17/205 506/7 |
| 2011/0184259 | A1 | 7/2011 | Alarcon et al. |
| 2012/0283358 | A1* | 11/2012 | Chatelier ............... G01N 33/5438 523/423 |
| 2014/0005606 | A1* | 1/2014 | Chen ............... A61K 9/0021 604/173 |
| 2014/0255311 | A1 | 9/2014 | Almutairi et al. |
| 2014/0275843 | A1 | 9/2014 | Piccirillo et al. |
| 2016/0015952 | A1* | 1/2016 | Omachi ............... A61M 37/0015 604/46 |

FOREIGN PATENT DOCUMENTS

| | | | | |
|---|---|---|---|---|
| WO | 2009/051703 | A1 | 4/2009 | |
| WO | 2010/051551 | A1 | 5/2010 | |
| WO | WO 2012125122 | A1 * | 9/2012 | ............ G01N 21/658 |
| WO | 2013/134401 | A2 | 9/2013 | |

OTHER PUBLICATIONS

Billingsley, et al., "Fluorescent Nano-Optodes for Glucose Detection", Anal. Chem., May 1, 2010, vol. 82(9), pp. 3707-3713, doi:10.1021/ac100042e.

Burton, et al., "Rapid Intradermal Delivery of Liquid Formulations Using a Hollow Microstructured Array", Pharm. Res., Jun. 26, 2010, pp. 1-10, doi:10.1007/sII095-010-0177-8.

Clark, et al., "Optochemical Nanosensors and Subcellular Applications in Living Cells", Mikrochimica Acta, 1999, vol. 131, pp. 121-128.

Monson, et al., "PEBBLE Nanosensors for In Vitro Bioanalysis", Biomedical Photonics Handbook, T. Vo-Dinh, editor, CRC Press, Boca Raton, FL (2003), www.umich.edu/-koplab/research2/CRC_Review_try3pr.pdf.

Ruckh, et al., "Polymer-Free Optode Nanosensors for Dynamic, Reversible, and Ratiometric Sodium Imaging in the Physiological Range", Scientific Reports, Nov. 28, 2013, vol. 3(3366), pp. 1-12, doi:10.1038/srep03366.

Soppimath, et al., "Biodegradable Polymeric Nanoparticles as Drug Delivery Devices", Journal of Controlled Release, 2001, vol. 70, pp. 1-20.

Dick, Lisa, "Pointing the Way", Innovations in Pharmaceutical Technology, 2014, Issue 50, pp. 1-3.

McIntyre, David, "Optical Tweezer Trapping of Fluorescent Ion Nanosensors", Oregon State University, pp. 1-2. [Retrieved from the Internet Oct. 21, 2014:<URL:http://www.physics.oregonstate.edu/-mcintyre/optodes.html>].

Prausnitz, Mark, "Polymer Microneedles", Laboratory for Drug Delivery, 2010, pp. 1-6. [Retrieved from the Internet Oct. 14, 2014:<URL:http://drugdelivery.chbe.gatech.edu/gallery_microneedles.html>].

Robinson-Avila, Kevin, "Sandia Develops Wrist Sensor for Electrolytes", Albuquerque Journal News, Jun. 16, 2014, pp. 1-2.

"Microneedle Drug Delivery Systems", 3M Drug Delivery Systems, pp. 1-3. [Retrieved from the Internet Oct. 14, 2014:<URL:http://solutions.3m/en_WW/3M-DDSD/Drug-Delivery-Systems/Technologies/Microneedle>].

"3M Hollow Microstructured Transdermal System", 3M Drug Delivery Systems, 2014, pp. 1-2.

"Technologies—Micro-Trans", Valeritas.

Cash, et al., "Nanosensors and Nanomaterials for Monitoring Glucose in Diabetes", Trends Mol Med., Dec. 2010, vol. 16(12), pp. 584-593. (Abstract only).

* cited by examiner

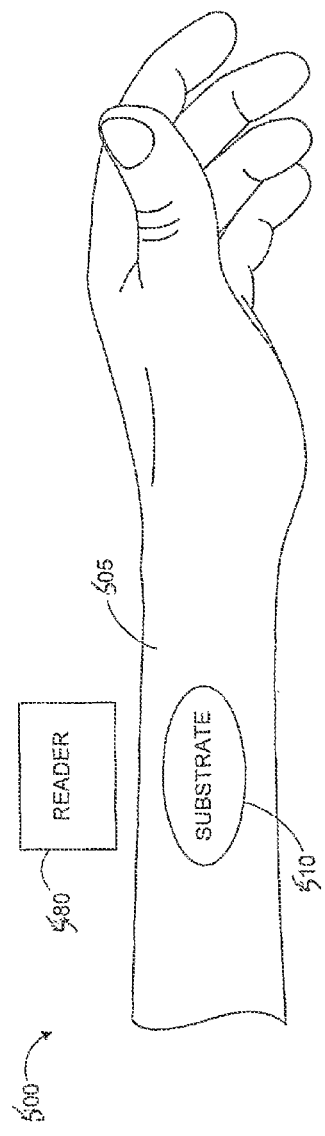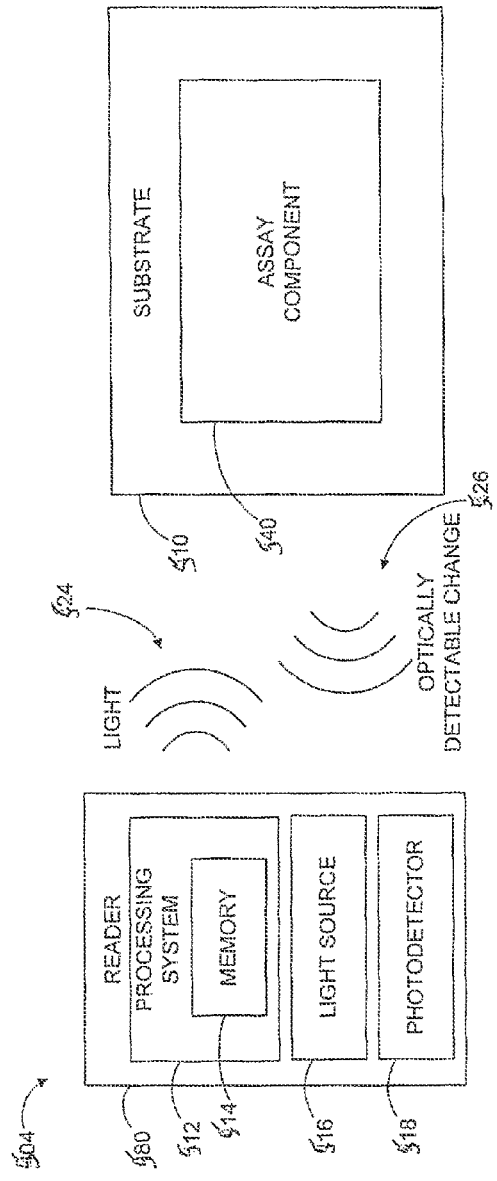

ANALYTE DETECTION SYSTEM AND METHOD FOR INTRADERMAL IMPLANTATION OF BIOCOMPATIBLE OPTODE NANOSENSORS

CROSS-REFERENCE

This application claims the benefit of priority from U.S. Provisional application Ser. No. 62/068,194, filed Oct. 24, 2014, which is incorporated by reference in its entirety.

BACKGROUND

Unless otherwise indicated herein, the materials described in this section are not prior art to the claims in this application and are not admitted to be prior art by inclusion in this section.

A number of scientific methods have been developed to detect and/or measure one or more analytes in a person's blood. The presence or absence of a physiologically relevant analyte in the blood, or the presence at a particular concentration or range of concentrations, may be indicative of a medical condition or the person's state of health. Physiologically relevant analytes may include enzymes, hormones, proteins, cells or other molecules.

In a typical scenario, a person's blood is drawn and sent to a lab where a variety of tests are performed to measure various analyte levels and parameters in the blood. The variety of tests may be referred to as "blood work," where the blood is tested for the presence of various diseases, or analyte levels such as cholesterol levels, etc. For most people, the blood tests are infrequent, and an abnormal analyte level indicative of a medical condition may not be identified for some time after the blood work is performed. Physiologically relevant analytes may also be present in a person's interstitial fluid. These analytes include sugars, salts, fatty acids, amino acids, coenzymes, hormones, neurotransmitters, and cell waste products. In analyzing for the presence and/or concentration of analytes from blood and other fluids, hypodermic needles are typically used which can cause pain, wounds, and potential infection sites in patients. A device and method that avoids the use of hypodermic needles and reduces the need for medical personnel and administration costs is desirable.

SUMMARY

One aspect of the present disclosure provides a system. The system includes a substrate comprising a (a) skin-mountable device, comprising: a plurality of micro-needles, each having a base end and a tip; a substrate attached to the base ends of the micro-needles, wherein the substrate is configured for attachment to an external skin surface such that the micro-needles penetrate into the skin; and nanosensors comprising nanoparticles having a detectable label and configured to interact with a specific analyte present in interstitial fluid; and (b) a reader device, wherein the reader device is configured to detect the target analyte via interaction with the skin-mountable device. In one embodiment, the substrate further includes an adhesive material for attaching the substrate to the external skin surface, for attaching the base ends of the micro-needles to the substrate, or both. In some embodiments, the adhesive is water-soluble such that the substrate can be detached from the base end of the micro-needles and from the external skin surface when water is applied. In other embodiments, the micro-needles can be arranged in a three-dimensionally spatially-controlled array. In yet other embodiments, the micro-needles are solid, hollow or porous. In some embodiments, the nanosensors can be bound to a surface of the micro-needles and/or can be encapsulated in the micro-needles. In some embodiments, the micro-needles comprise hollow or porous spaces comprising the nanosensors. In other embodiments, the micro-needles, nanosensors, or both are bio-degradable.

In other embodiments, the substrate includes a component configured to undergo an optically-detectable change upon interaction with an analyte. The optically-detectable change may involve a change in at least one of optical absorption, reflectivity, or fluorescence. The substrate can be used in conjunction with a reader device configured to detect the optically-detectable change. The reader device may include an excitation light source configured to direct light toward the substrate, and a photodetector configured to detect light from the substrate. The detected optical change can be used to determine the presence/absence of an analyte or the concentration of an analyte.

In another aspect, the present disclosure provides a device. The device includes a a plurality of micro-needles, each having a base end and a tip; a substrate attached to the base ends of the micro-needles, wherein the substrate is configured for attachment to an external skin surface such that the micro-needles penetrate into the skin; and nanosensors comprising nanoparticles having a detectable label and configured to interact with a target analyte present in interstitial fluid.

In another aspect, the present disclosure provides a method. The method includes: transmitting incident light from a reader device to a skin-mountable device, wherein the skin-mountable device comprises (i) a plurality of micro-needles, each having a base end and a tip, (ii) a substrate attached to the base ends of the micro-needles, wherein the substrate is configured for attachment to an external skin surface such that the micro-needles penetrate into the skin, and (iii) nanosensors comprising nanoparticles having a fluorophore and configured to interact with a target analyte present in interstitial fluid; receiving, by the reader device, fluorescence light emitted by the nanosensors interacting with the target analyte in response to the incident light; and detecting the target analyte based on the fluorescence light received by the reader.

In another aspect, the present disclosure provides another method. The method includes: attaching a skin-mountable device to the external skin surface of living body, the skin-mountable device comprises (i) a plurality of micro-needles, each having a base end and a tip, (ii) a substrate attached to the base ends of the micro-needles, wherein the substrate is configured for attachment to an external skin surface such that the micro-needles penetrate into the skin, and (iii) nanosensors comprising nanoparticles having a fluorophore and configured to interact with a target analyte present in interstitial fluid, wherein the device further comprises an water-soluble adhesive material for attaching the substrate to the external skin surface and for attaching the base ends of the micro-needles to the substrate; applying water to the skin-mountable device so as to dissolve the adhesive material; detaching the substrate from the external skin surface and the base ends of the micro-needles, leaving detached micro-needles embedded in the skin; transmitting incident light from a reader device to the detached micro-needles; receiving, by the reader device, fluorescence light emitted by the nanosensors interacting with the target analyte in response to the incident light; and detecting the target analyte based on the fluorescence light received by the reader.

In another aspect, the present disclosure provides yet another method. The method includes: attaching a skin-mountable device to the external skin surface of living body, the skin-mountable device comprises (i) a plurality of micro-needles, each having a base end and a tip, (ii) a substrate attached to the base ends of the micro-needles, wherein the substrate is configured for attachment to an external skin surface such that the micro-needles penetrate into the skin, and (iii) nanosensors comprising nanoparticles having a fluorophore and configured to interact with a target analyte present in interstitial fluid; injecting the nanosensors through the micro-needles into the skin; removing the skin-mountable device; transmitting incident light from a reader device to the injection site; receiving, by the reader device, fluorescence light emitted by the nanosensors interacting with the target analyte in response to the incident light; and detecting the target analyte based on the fluorescence light received by the reader. In some embodiments, the device further comprises a reservoir including the nanosensors.

In other embodiments, the micro-needles are not dissolvable or degradable and are coated with dissolvable or degradeable coating of a polymer and the nanosensors.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 5A is an example system that includes a skin-mountable device and a proximate reader, in accordance with an example embodiment FIG. 5B is a block diagram of a skin-mounted optical sensor system operated by a reader device capable of detecting an optically-detectable change in a substrate, in accordance with an example embodiment.

DETAILED DESCRIPTION

I. Overview

Figure 1:
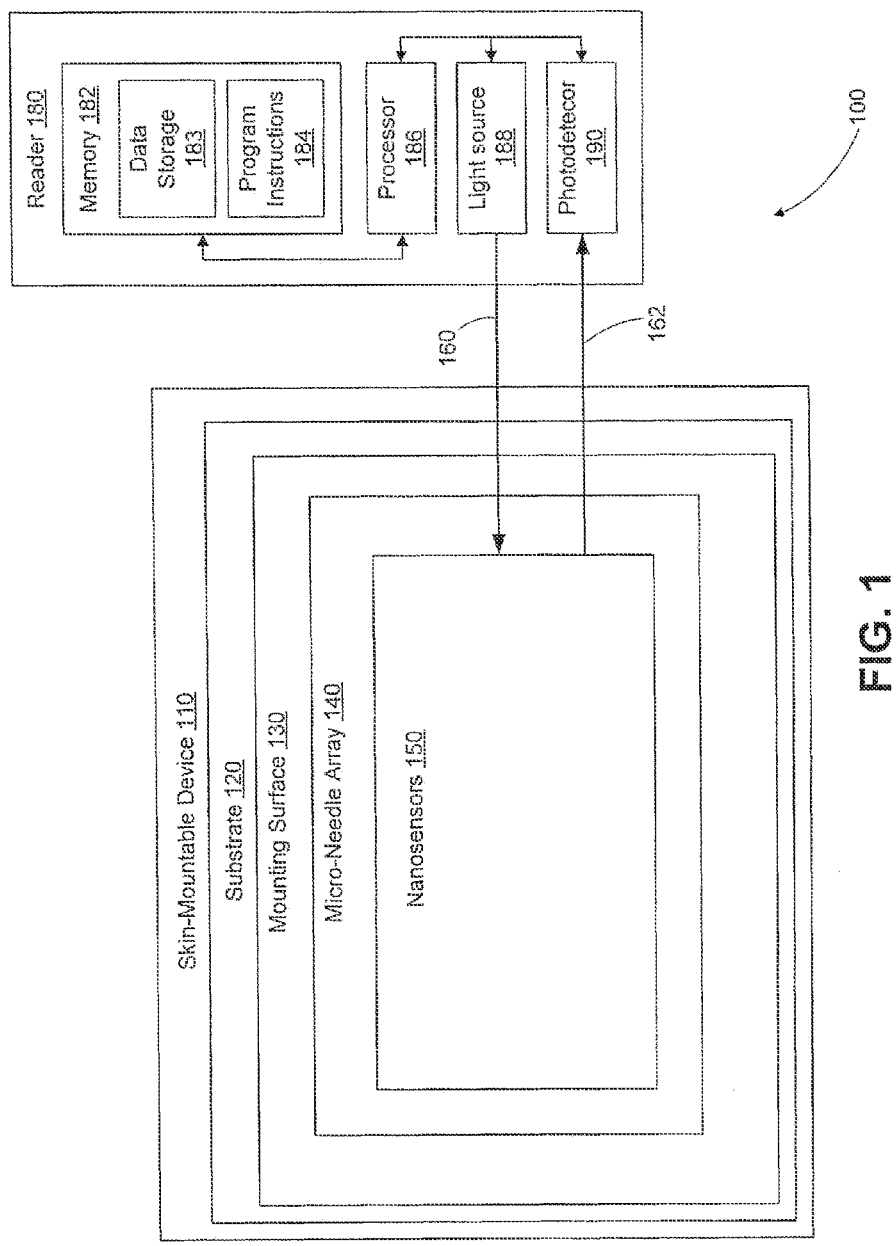
FIG. 1 is a block diagram of an example system that includes a skin-mountable device in wireless communication with a reader device, in accordance with an example embodiment.

A system for monitoring analyte levels can include a skin-mountable device and a reader device. The skin-mountable device may include a plurality of micro-needles that can penetrate into the epidermis, intradermis, or dermis, a polymer backing attached to the micro-needles, and optode nanosensors configured to interact with an analyte present in interstitial fluid in the epidermis, intradermis, or dermis. The reader device can detect the analyte by optically interrogating the nanosensors. Alternatively or additionally, the skin-mountable device may include its own optical sensor, control electronics, and an antenna for wireless communication with the reader. The control electronics can operate the sensor to perform readings and can operate the antenna to wirelessly communicate the readings from the sensor to the reader device via the antenna.

A "skin-mountable" device or substrate can be attached to an "external skin surface," i.e., the epidermis, intradermis, or dermis, and in that attached position the micro-needles can penetrate into subsurface skin tissue, i.e. the epidermis, intradermis, or dermis. In this way, the micro-needles may have direct contact with interstitial fluid. In one embodiment, the substrate can be a transdermal micro-needle patch.

Interstitial fluid contains a variety of inorganic electrolytes (e.g., $Na^+$, $Ca^{2+}$, $K^+$, bicarbonate, $Cl^-$), organic components (e.g., glucose, urea, creatinine), and so on that can be used to diagnose health states. A system including the above-mentioned nanosensors can be configured to measure one or more of these analytes can thus provide a convenient platform useful in diagnosing and/or monitoring health states. For example, a system can be configured to sense glucose and can be used by diabetic individuals to measure/monitor their glucose levels.

An external reader device or "reader" can optically interrogate the skin-mountable device. For example, the reader can transmit incident light that excites a fluorophore in the nanosensors and receive fluorescence light from the nanosensors interacting with the target analyte. The reader may detect the target analyte (and may determine the concentration of the target analyte in the interstitial fluid) based on the fluorescence light.

The analyte concentration information can be sent from the reader to a display device. The display device could be, for example, a wearable, laptop, desktop, handheld, or tablet computer, a mobile phone, or a subsystem of such a device. In some embodiments, the reader is also the display device. The display device can include a processing system; e.g., a central processing unit (CPU), and a non-transitory computer readable medium configured to store at least program instructions. One example of a wearable computer is a head-mountable display (HMD). The HMD can be a device that is capable of being worn on the head and places a display in front of one or both eyes of the wearer. The display device can store the data received from the reader, perhaps process the data, and generate display(s) based on the received and/or processed data.

In some embodiments, the reader is a wearable device, such as an arm or wrist band, and can be worn directly over the skin-mountable device.

II. Example System

FIG. 1 is a block diagram of a system 100 that includes a skin-mountable device 110 and a reader 180. The skin-mountable device 110 includes a substrate 120 that is configured to be mounted to an external body surface (i.e., skin). The substrate 120 could be formed from a polymeric material, for example. The substrate 120 has a mounting surface 130 for mounting to the skin. Attached to the mounting surface 130 of the substrate is a micro-needle array 140. The micro-needle array 140 is configured to penetrate into the skin (e.g., into the intradermis when the substrate 120 is mounted to the skin. Disposed on or within the micro-needles of the array 130 are nanosensors that are sensitive to a target analyte present in interstitial fluid in the epidermis, intradermis, or dermis. The nanosensors are in the form of nanoparticles and include a detectable label (e.g., fluorophore). The optical properties of the detectable label undergo a detectable change (e.g., a change in fluorescence) when the nanosensor interacts with the target analyte.

Reader 180 can also include a computing system with a processor 186 in communication with a memory 182. Memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the substrate 110 and/or reader 180), etc. The memory 182 can also include program instructions 184 for execution by the processor 186 to cause the reader 180 to perform processes specified by the instructions 184. For example, the program instructions 184 can cause reader 180 to perform any of the operations described herein.

As shown, the reader device 180 can include a light source 188 configured to transmit incident light 160 to the skin-mountable device 110 and a photodetector 190 configured to receive light 162 from the skin-mountable device 110. The incident light 160 can be used to optically interrogate the nanosensors 150 so as to detect interaction of the nanosensors 150 with the target analyte in the interstitial fluid. For example, the incident light can include a wavelength that excites a fluorophore in the nanosensors 150 such that the nanosensors 150 emit fluorescence light. The fluorescence light can be included in the received light 162 and detected by the photodetector 162. Based on the light from the nanosensors 150 that is detected by the photodetector 160, the reader 180 can detect the target analyte. Moreover, the detection could be quantitative. For example, an intensity, wavelength, or other characteristic of the received light 162 may be indicative of the concentration of the target analyte in the interstitial fluid.

The components of the skin-mountable device 110 may be transparent to the incident light 160 and the light 162 emitted by the nanosensors in response to the incident light 160.

III. Illustrative Micro-Needle Sensor

In one aspect, a transdermal or skin patch is provided. The skin patch having an array of microfabricated micro-needles can be used as a minimally invasive device for detecting target analytes in interstitial fluid or for delivering nanosensors into the skin for detecting target analytes. Thus, in one embodiment, the micro-needles can act as a sensing element. A skin patch having micro-needle array would allow for a spatially-controlled array of optode nanosensors to be implanted at a controlled depth into the epidermis, intradermis, or dermis simultaneously, allowing for an optimal depth to be selected, depending on the individual's specific physiology, to sample interstitial fluid. As defined herein, "optode nanosensors" or "nanosensors" refers to nanosensors that emit an optical signal, e.g. fluorescent signal, upon detection of an analyte.

In another embodiment, the micro-needle array can act as a delivery system in a method for delivering optode nanosensors directly into the epidermis, intradermis, or dermis in a spatially-controlled manner. In some embodiments, the micro-needle array having nanosensors can be readily removed by simply removing the transdermal patch. In other embodiments, the micro-needle, the nanosensors, or both are made from biocompatible polymers. In other embodiments, the micro-needle array, the nanosensors, or both are made of biodegradable polymers. In other embodiments, the implanted micro-needle array having nanosensors can be left in place in the skin where both the micro-needle array and nanosensors are eventually degraded and absorbed.

The geometry of the micro-needles can be optimized to have a uniform cross-sectional area for accurate fluorescence detection as a function of depth. Furthermore, the micro-needle array would allow for single analyte or multiplex detection of different analytes such as potassium ions, sodium ions, glucose, using different nanosensors that are spatially well-defined. Furthermore, the micro-needle patch avoids the use of hypodermic needles for implantation as well as reduces the need for medical personnel and associated administration costs. The transdermal patch can be fabricated from or coated with FDA-approved biocompatible material to mitigate any inflammatory response. In one embodiment, the patch material can also be optically transparent to avoid interference with detection of the response signal by a photodetector.

In one embodiment, the transdermal patch includes an array of solid or hollow microfabricated micro-needles, the micro-needles having at least one type of nanosensors. The nanosensors can detect target analyte in interstitial fluid. The nanosensors in a polymer matrix can be coated or bound covalently or non-covalently to at least a portion of a surface of the micro-needles. The micro-needles, the nanosensors, and/or the polymer matrix can be biodegradable.

In another embodiment, the transdermal patch includes an array of hollow microfabricated micro-needles conjugated to nanosensors. The nanosensors in a polymer matrix can be coated or bound covalently or non-covalently to the inner wall surface of the hollow micro-needles or can fill at least a portion of the internal hollow space of the micro-needle. The micro-needles, the nanosensors, and/or the polymer matrix can be biodegradable.

In another embodiment, the transdermal patch includes an array of porous microfabricated micro-needles conjugated to nanosensors. The nanosensors in a polymer matrix can be coated or bound covalently or non-covalently to at least a portion of the wall surfaces of pores in the micro-needles. The micro-needles, the nanosensors, and/or the polymer matrix can be biodegradable.

In another embodiment, the microfabricated micro-needles can be biodegradable.

In another embodiment, the microfabricated micro-needles can be formed from a polymer matrix that includes the nanosensors. The polymer matrix, the nanosensors, or both can be biodegradable.

In another embodiment, each micro-needle can be associated with a plurality of types of nanosensors, each type directed to a specific target analyte, to provide a spacially defined micro-needle array to allow for the detection of a multitude of different analyltes such as Na+, K+, glucose, etc. in a controlled spatial array.

1. The Micro-Needle Sensor

The micro-needle sensor can include at least three components: (i) a plurality of micro-needle(s), (ii) a substrate to which the base of the micro-needles is secured or integrated, and (iii) at least one type of nanosensor. Optionally, a collection chamber for receiving interstitial fluid or a reservoir for delivering materials can be included. In one embodiment, the nanosensor can be coated, layered, or bound covalently or non-covalently to a surface of micro-needles. In some embodiments, the nanosensors can be suspended in a polymer matrix or gel contained within the interior hollow space of a hollow or porous micro-needle. In other embodiments, the nanosensors embedded in solid micro-needles. In another embodiment, at least one fluid collection chamber can be associated with the device for collecting interstitial fluid during detection of target analytes. In another embodiment, at least one reservoir can be associated with the device to hold a nanosensor-hydrogel slurry for subsequent injection by the micro-needles into the skin. Typically, the micro-needles are provided as a three-dimensional array, in contrast to a device with a single needle or row of needles. The micro-needle device can be adapted to be a single-use, disposable device, or can be adapted to be fully or partially reusable.

a. Substrate

The substrate of the device can be constructed from a variety of materials, including metals, ceramics, semiconductors, organics, polymers, and composites. In one embodiment, the substrate can constructed with materials that are optically invisible so as to not interfere with optical detection of target analytes using the nanosensors.

The substrate includes an underlying surface to which the micro-needles are attached or integrally formed. A fluid collection chamber and/or reservoir can be attached to the substrate or formed (e.g., as part of the substrate) to communicate directly with the base of the micro-needles. In one embodiment, the substrate can be flexible so that it deforms with the skin and can assume a variety of shapes such as linear or curve shape to adapt to the elasticity of the skin.

In another embodiment, the substrate includes an adhesive material to temporarily secure the device to the surface of the biological barrier. The adhesive can be essentially anywhere on the device to facilitate contact with skin. For instance, the adhesive can be anywhere on the substrate surface that contacts skin such as the surface of the substrate between the micro-needles near the base of the micro-needles. In one embodiment, the adhesive material is optically invisible so as to not interfere with the detection of the nanosensors.

In another embodiment, the substrate includes a water soluble adhesive material to temporarily secure the needles onto the substrate and to secure the device to the surface of the skin. After application of the micro-needle device to skin, water is then used to dissolve the adhesive and the substrate can be detached from the skin, releasing the needles into the skin. The needles remain stationary in a fixed position and this can allow for improved optical properties for detection. In some embodiments, the micro-needles are biodegradable so that they will degrade and disappear at a pre-determined time, e.g., three days or one week. In other embodiments, the nanosensors are biodegradable as well.

b. Micro-Needle Array

The array of micro-needles can function as a sensing element and/or a conduit. Conduit micro-needles can have a porous or hollow shaft. As used herein, the term "porous" means having pores or voids throughout at least a portion of the micro-needle structure, sufficiently large and sufficiently interconnected to permit passage of fluid and/or solid materials through the micro-needle. As used herein, the term "hollow" means having one or more substantially annular bores or channels through the interior of the micro-needle structure, which have a diameter sufficiently large to permit passage of fluid and/or solid materials through the micro-needle. The annular bores may extend throughout all or a portion of the needle in the direction of the tip to the base, extending parallel to the direction of the needle or branching or exiting at a side of the needle, as appropriate. One skilled in the art can select the appropriate porosity and/or bore features required for specific applications. For example, one can adjust the pore size or bore diameter to permit or regulate passage of the particular material to be transported through the micro-needle device.

In one embodiment, the micro-needles are solid, hollow, and/or porous. When functioning as a sensing element, the nanosensors can be encapsulated in a polymer matrix and coated, layered, or bound covalently or non-covalently onto the internal and/or external wall surfaces of the micro-needles or can be placed in the hollow or porous spaces of the micro-needles.

The micro-needles of the device can be constructed from a variety of materials, including metals, ceramics, semiconductors, organics, polymers, and composites. Suitable materials of construction include, without limitation, pharmaceutical grade stainless steel, gold, titanium, nickel, iron, tin, chromium, copper, palladium, platinum, alloys of these or other metals, silicon, silicon dioxide, and polymers. Representative polymers include biodegradable polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly (lactide-co-caprolactone). Representative non-biodegradable polymers include polycarbonate, polymethacrylic acid, ethylenevinyl acetate, polytetrafluoroethylene (TEFLON™), and polyesters. In one embodiment, the micro-needles can be constructed from materials that are optically invisible and do not interfere with the optical detection of target analytes.

In one embodiment, the micro-needles can have the mechanical strength to remain intact for sensing target analyte and/or for serving as a conduit for the collection of biological fluid or for injecting a nanosensor slurry, while being inserted into the skin, while remaining in place for up to a number of days, and while being removed. In other embodiments where the micro-needles are formed of biodegradable polymers, the micro-needle can remain intact at least long enough for the micro-needle to serve its intended purpose (e.g., its conduit function or sensing function). The micro-needles can be sterilizable using standard methods, such as ethylene oxide treatment or gamma irradiation.

The micro-needles can have straight or tapered shafts. A hollow micro-needle that has a substantially uniform diameter, which needle does not taper to a point, is referred to herein as a "microtube." As used herein, the term "micro-needle" includes both microtubes and tapered needles unless otherwise indicated. In one embodiment, the diameter of the micro-needle is greatest at the base end of the micro-needle and tapers to a point or tip at the end distal the base. The micro-needle can also be fabricated to have a shaft that includes both a straight (untapered) portion and a tapered portion.

The cross-sectional dimensions of the micro-needles can be between about 1 µm and 500 µm, usually between 10 µm and 100 µm. The outer diameter can be between about 10 µm and about 100 µm, and the inner diameter can be between about 3 µm and about 80 µm. The length of the micro-needles can be typically between about 10 µm and 1 mm, usually between 100 µm and 500 µm or between 150 µm and 350 µm. The length is selected for the particular application, accounting for both an inserted and uninserted portion. One skilled in the art will understand that the proper selection of the length and diameter of the micro-needles depends on the skin depth that provides the greatest access of interstitial fluid and that pain avoidance from the micro-needles interacting with the nerve endings and capillaries in the dermis is desirable.

An array of micro-needles can include a mixture of micro-needles having, for example, various lengths, outer diameters, inner diameters, cross-sectional shapes, and spacings between the micro-needles. Generally, the micro-needles are sized to avoid or minimize contact with nerve endings in the biological tissue, such as the dermis, thereby eliminating or reducing pain when the micro-needles are inserted, for example into the skin.

The micro-needles can be oriented perpendicular or at an angle to the substrate. Preferably, the micro-needles are oriented perpendicular to the substrate to provide structural strength and to permit ease of insertion into the tissue. An array of micro-needles can include a mixture of micro-needle orientations, heights, spacings, or other parameters. This variation in an array can be useful, for example, if different micro-needles are to provide different sensing or insertion functions.

The micro-needle devices can be made by any suitable microfabrication processes, by creating small mechanical structures in silicon, metal, polymer, and other materials. These microfabrication processes are based on well-established methods used to make integrated circuits, electronic packages and other microelectronic devices, augmented by additional methods used in the field of micromachining. The micro-needle devices can have dimensions as small as a few nanometers and can be mass-produced at low per-unit costs. Representative microfabrication processes that may be used in making the micro-needles disclosed herein include lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, and laser ablation (including projection ablation).

In one embodiment, the interaction with the target analyte can occur in or on the micro-needle. In this embodiment, the nanosensor is located in or on the micro-needle, contacts the interstitial fluid containing the analyte, and undergoes a detectable change as a result of interaction with the analyte. The detectable change may be indicated optically, e.g., based on fluorescence emitted by the nanosensors when optically interrogated. The nanosensors can be located on the micro-needle surface, inside the surface of a hollow or porous micro-needle, and/or embedded in the micro-needle. For example, nanosensors encapsulated in a polymer gel can be coated onto the external surface of hollow or solid micro-needles, distributed within the pores of porous micro-needles, or line or fill the bore(s) of hollow micro-needles.

Figure 2A:
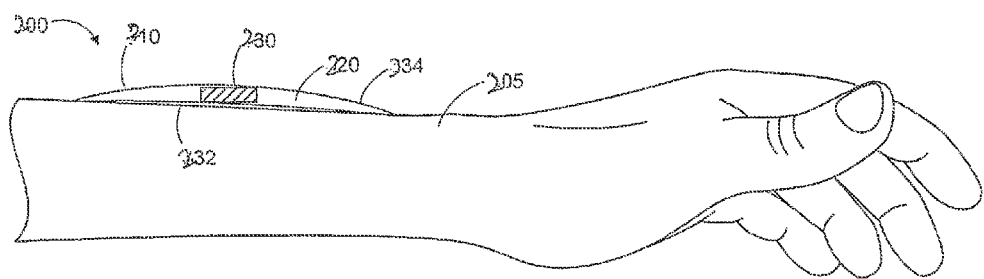
FIG. 2A is a side cross-section view of an example skin-mountable device while mounted to the surface of an arm.
Figure 2B:
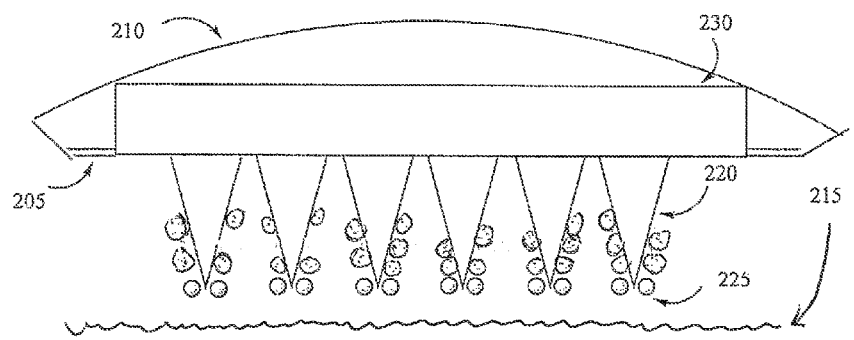
FIG. 2B is a side cross-section view enhanced to show the assay component of the example skin-mountable device when mounted as shown in FIG. 2A.
Figure 2C:
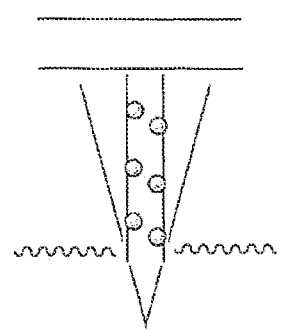
FIG. 2C is a side cross-section view enhanced to show another embodiment of an assay component the example skin-mountable device when mounted as shown in FIG. 2A.
Figure 2D:
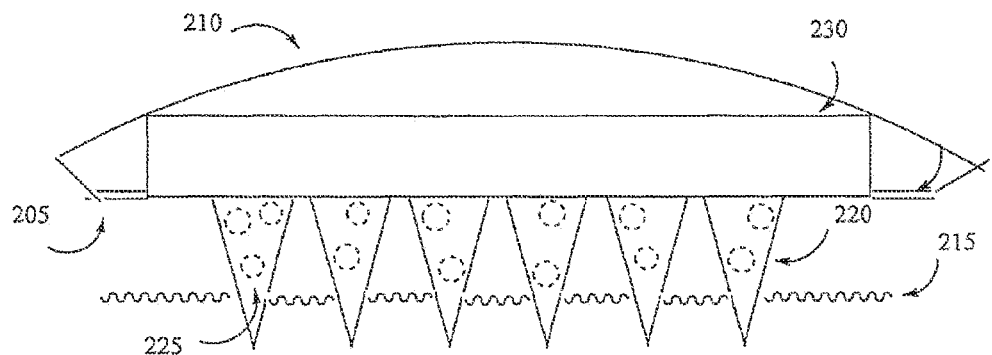
FIG. 2D is a side cross-section view enhanced to show a further embodiment of an assay component the example substrate when mounted as shown in FIG. 2A.

FIG. 2A shows the cross-sectional views of 200 with the substrate 210 mounted on the skin 205 with an inward-facing surface 232 and an outward-facing surface 234. It is noted that relative dimensions in FIG. 2A are not necessarily to scale, but have been rendered for purposes of explanation only in describing the arrangement of the example skin-mountable substrate 210. The substrate 210 can have an optode nanosensor as assay component 230 configured to undergo an optically-detectable change upon interaction with an analyte. In some examples, the optically-detectable change may involve a change in optical absorption, reflectivity, and/or fluorescence. The assay component 230 may be attached or partially embedded in substrate 210. FIG. 2B illustrates a cross sectional view of an embodiment of a substrate 210 including micro-needles 220, attached to substrate 230, where the nanosensor is coating a portion of the external surface of the micro-needles. The micro-needles can be hollow, solid or porous. FIG. 2C illustrates a cross sectional view of another embodiment of a micro-needle device 210 including micro-needle 222, attached to substrate 230, having a hollow bore 221 where the nanosensor 225 is coating a portion of the surface of the hollow bore 221. In FIG. 2D, nanosensors material 225 are embedded or encapsulated within a solid micro-needle 226. Solid micro-needles can also hold or contain nanosensors material as in FIG. 2B or 2D. Various micro-needle types and nanosensors can be used in different combinations within a device array.

In one embodiment, the micro-needle device provides a single-use collection means. In this design, the micro-needle array device is used to extract a single or series of measurements over a period of time and then is detached from the skin and disposed of. Sensing information or signals can be transferred optically, e.g., refractive index or fluorescence.

The micro-needle can function as a conduit for fluids, solutes, electric charge, light, or other materials. In one embodiment, hollow micro-needles can be filled with a substance, such as a gel, that has a sensing functionality, e.g., nanosensors, associated with it. In an application for sensing based on the binding of a substrate or reaction mediated by an enzyme, the substrate or enzyme or both can be immobilized on or on the needle.

c. Optode Nanosensors

In one embodiment, the optode nanosensors can emit light, e.g., fluorescence, at different intensities in the presence of a target analyte, such as glucose. As indicated above, the analyte can be any biomolecule or ion of interest, e.g., glucose, sodium, potassium, calcium, chloride, or a combination thereof. Suitable but non-limiting examples of nanosensors suitable for use in the devices, systems, and methods as described herein are described in Balaconis et al., Biodegradable optode-based nanosensors for in vivo monitoring. *Anal Chem.* 2012 Jul. 3; 84(13):5787-93, which is hereby incorporated by reference in its entirety. Additional nanosensors suitable for use in the present system and methods include, copper and copper oxide nanowires, porous films as well as nanoflowers and nanorods, nano-structured copper oxide/copper oxalate, nanoparticles composed of silver, gold, nickel, and nickel/palladium, such as gold nanowires, nickel hydroxide nanocomposites, boron-doped diamond nanorods, platinum/lead nanoporous networks, palladium nanoparticles, polymeric nanoparticles, and fluorescent polymeric nanosensors. See, e.g., Cash and Clark, Trends Mol Med. Sep. 23, 2010; 16(12): 584-593, which is incorporated herein by reference.

Fluorescent polymeric nanosensors are particularly useful in detecting target analytes such as $Na^+$, $K^+$, $Cl^-$, glucose, urea, creatinine, and bicarbonate. Fluorescent nanosensors are a modular family of sensors that can continuously monitor in vivo physiological parameters, including by not limited to oxygen, pH, ammonia, nitrate, nitrite, and sulfate. The sensors are approximately 100 nm in diameter, and specific nanosensor formulation can emit a reversible, concentration-dependent fluorescent signal.

In one embodiment, the nanosensor can be a sensor material comprised of a (i) quantum dot or a fluorescent dye as a signal source that fluoresces at a first wavelength, (ii) a chromophore that absorbs photons of a first wavelength in one state and does not absorb photons of the first wavelength in a second state, and (iii) an ionophore which selectively associates with specific ions or groups of ions, all which are embedded in a polymer including a plasticizer. An additive, e.g., optically-inactive hydrophobic charge-carrying molecule, for facilitating ion exchange within the sensor's hydropobic core and providing charge neutrality within the sensor may be included. The polymer imparts mechanical stability while the plasticizer allows the three encapsulated sensing components to diffuse within an individual nanoparticle. In monitoring ionic analytes, the chromoionophore changes state in response to proton concentration, e.g, the protonated chromoionophore is one state while the deprotonated chromoionophore is a second state. To monitor a specific analyte, an ionophore that selectively associates with specific ions or group of ions is included in the nanosensor. Once the ionophore associates with a cationic analyte, e.g., Na+ associates with a Na+ selective ionophore, for instance, protons are displaced from the sensor to equilibrate charge, altering the state of the chromoionophore. The fluorescence emitted from the nanosensor indicates the state of the chromoionophore which correlates to the presence and/or concentration of the ionic analyte. For a review of fluorescent polymeric nanosensors and methods of preparation, see U.S. Pat. No. 8,263,358; PCT/US20013/029396; Balaconis et al, Anal. Chem., 2012, Vol. 84(13), pp. 5787-5793; Clark et al., Mikrochim. Acta 131, pp. 121-128 (1999); Monson et al. "PEBBLE nanosensors for in vitro bioanalysis" (www.umich.edu/~koplab/research2/CRC_Review_tr33pr.pdf); Billingsley et al, Anal. Chem, (2010), Vol. 82(9), pp. 3707-3713 (doi: 10.1021/ac100042e) which are incorporated by reference in their entirety.

In one embodiment, nanosensors that are biocompatible and biodegradable and that do not induce an inflammatory response upon implantation into tissue are provided. As the intradermal environment is one of the most immunogenic tissues in the body, implantation of nanosensors will most likely induce an inflammatory response and subsequent fibrotic tissue deposition to form a fibrotic capsule which could severely affect the performance of the nanosensors. Depending on the implantation time-frame, the formation of a fibrotic capsule can dampen the fluorescence signal to the detector as well as and decrease the diffusion of ions or other analytes that reach the nanosensors. Therefore, biocompatible and biodegradable materials are desired in manufacturing the nanoparticles. Furthermore, such materials can be hydrophobic and/or with degradation products that do not alter the local pH. Suitable but non-limiting example of sensor material that can be used to make biocompatible/biodegradable nanosensors include polycaprolactone (PCL), pluronics (F-127) and citroflex, a citric acid based plasticizer. For a description of suitable sensor material for making biocompatible/biodegradable nanosensors for in vivo use can be found in Balaconis et al., Anal Chem. 2012 Jul. 3; 84(13):5787-93, which is incorporated by reference in its entirety;

In one embodiment, the polymer is biocompatible. The term biocompatible polymers includes polymers that are neither themselves toxic to the host, e.g., a cell, human, or animal) nor degrades at a rate that produces monomeric or oligomeric subunits or byproducts at toxic concentrations to the host. Representative examples of suitable biocompatible polymers include, without limitation, poly (caprolactone) (PCL), ethylene vinyl acetate polymer (EVA), poly(ethylene glycol)(PEG), poly(vinyl acetate)(PVA), poly(lactic acid) (PLA), poly(glycolic acid)(PGA), poly(lactic-co-gylcolic acid)(PLGA), chitosan, alginate, polylysine, collagen or mixtures thereof In this embodiment, a biocompatible plasticizer may be used with the polymer and includes materials which are soluble or dispersible in the relevant polymer which increases the flexibility of the polymer matrix, and which, in the amounts employed, are biocompatible. Suitable plasticizers include, without limitation, dioctyl sebacate (DOS), poly(glycerol sebacate)(PGS), and acetyl tri-n-butyl citrate. Representative examples of suitable polymers and plasticizers include those described in U.S. Pat. Nos. 2,784,127; 4,444,933; and 8,263,358.

In another embodiment, florescence nanosensors are combined with a catalytic agent that catalyzes a reaction in which a target substrate and/or a co-substract is converted into one or more products. This expands the range to detectable target analytes to include biological molecules such as glucose. This is embodiment, the target can be the target substrate, the co-substrate, or at least one of the one or more products and the nanosensor is sensitive to the analyte such that the nanosensor emits a fluorescent signal upon detecting the analyte. In one embodiment, the catalytic agent is an enzyme. Non-limiting representative examples of catalytic agents include glucose oxidase, diamino oxidase, acetylcholine esterase, cholesterol oxidase or glutamate dehydrogenase. Enzyme-based sensors can recognize a broad range of target substrates with high recognition specificity such as glucose. In one embodiment, the enzyme is an oxidase. For instance, glucose oxidase catalytically oxidizes glucose into gluconic acid, which lowers the pH, and the measured pH change based on optical emission correlates to glucose concentration. In some embodiments, the nanosensor and catalytic agent can be embedded in a polymer matrix such as a hydrogel. Cofactors and other components support the catalytic agents can be included.

In another embodiment, the catalytic agent can be a non-enzymatic protein. In another embodiment, the catalytic agent is a non-biological component such as lipophilic boronic acid derivatives that can serve as a glucose recognition elements. See, for instance, Billingsley et al. *Anal. Chem*. (2010), Vol. 82(9), pp. 3707-3713.

The nanosensor materials can be sized or shaped into any suitable configurations that can be achieved using the polymer. The sensor materials can be spun, sprayed or evaporated onto any surface of the micro-needles including the outside surface wall or interior surface of the micro-needles to produce a coating including the nanosensors.

In another embodiment, the nanosensor may include a targeting moiety such as a member of a specific binding pair such as a ligand, a receptor, an antibody or aptamer. In some embodiments, the targeting moiety can be bound to the polymer matrix.

d. Collection Chamber

In one embodiment, an optional fluid collection chamber can be included to collect interstitial fluid. The fluid collection chamber is selectably in connection with the micro-needle bores or pores, such that interstitial fluid can flow from the tissue surrounding the micro-needle, through the micro-needle, and into the collection chamber. Typically, the collection chamber is attached to, or integrated into, the substrate. The chamber should function to contain a biological fluid sample so as to permit analysis within or on the micro-needle device.

The collection chamber can be substantially rigid or readily deformable. The collection chamber can be formed from one or more polymers, metals, ceramics, semiconductor, or combinations thereof. In a preferred embodiment, the collection chamber contains a porous or absorbent material, such as a sponge, gel, or paper or polymeric strip. The material can be permanently contained or removable, and can function as a separate diagnostic element or substrate for use in analytical devices. The chamber can initially be empty or can contain a gas or one or more reagents in any form (e.g., liquid or solid particles).

In one embodiment, the collection chamber is formed of an elastic material, such as an elastomeric polymer or rubber. For example, the collection chamber can be a collapsed balloon-like pouch that expands when the biological fluid is drawn into the collection chamber.

In another embodiment, the collection chamber of a micro-needle device can include a plurality of compartments that are temporarily or permanently isolated from one another and/or from a portion of the micro-needles in an array. The device can, for example, be provided to collect or sense through different needles at different rates or at different times into the different compartments.

e. Reservoir

In one embodiment, the micro-needle device can include a reservoir for delivering a material, e.g., a slurry of nanosensors in a hydrogel, into the skin. The reservoir can be in communication with the micro-needles and can be attached to the substrate by any suitable means. In one embodiment, the reservoir is attached to the back of the substrate (opposite the micro-needles) around the periphery using an adhesive agent. A gasket may also be used to facilitate formation of a fluid-tight seal.

In another embodiment, the reservoir contains a slurry having nanosensors and hydrogels for direct delivery through the micro-needles into skin (e.g., to form a tattoo). The reservoir can be a substantially rigid or readily deformable hollow vessel or chamber or can be a porous matrix. The reservoir can be formed from a variety of materials that are compatible with the nanosensors and hydrogels contained therein. Suitable but non-limiting examples of materials include natural and synthetic polymers, metals, ceramics, semiconductors, and composites. In one embodiment, the reservoir is a standard syringe.

The micro-needle device can include one or a plurality of chambers for storing materials to be delivered. In the embodiment having multiple chambers, each can be in fluid connection with all or a portion of the micro-needles of the device array. In one embodiment, at least two chambers are used to separately contain different types of nanosensors in order to allow for detection of multiple different target analytes. In another embodiment, a single device is used to deliver different types of nanosensors to different portions of the micro-needles of the device array, which are stored separately in different chambers. In this embodiment, the rate of delivery of each nanosensor can be independently controlled.

In one embodiment, the reservoir should be in direct contact with the micro-needles and have holes through which the nanosensor slurry could exit the reservoir and flow into the interior of hollow or porous micro-needles.

In another embodiment for nanosensor delivery, the reservoir is selectably in connection with the micro-needle bore, such that the reservoir contents can flow from the reservoir and out through the micro-needle tip, into the target tissue. Typically, it is attached to or integrated into, the substrate, either integrally (as in a one-piece device) or at the moment of drug delivery (as with a Luer-lock type device). The reservoir can provide a suitable, leak-free storage of the nanosensor before it is to be delivered.

IV. Microinjection of Optode Nanosensors

Figure 3:
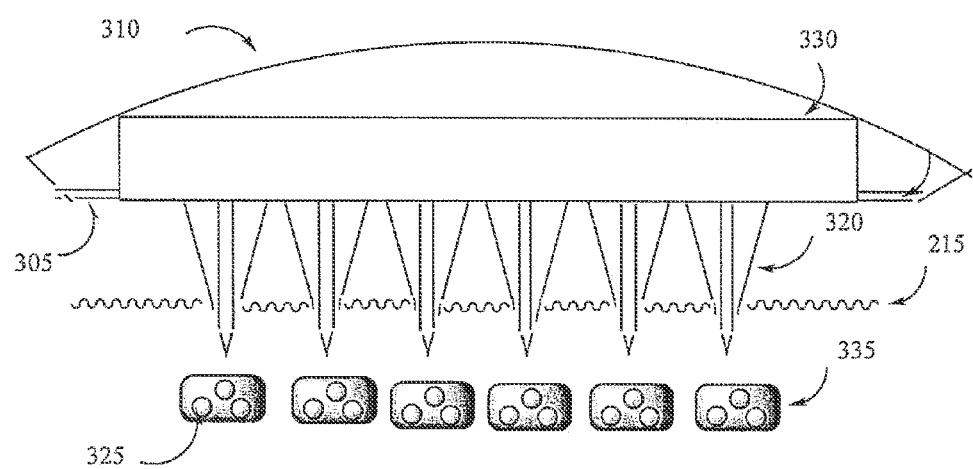
FIG. 3 is a side cross-section view enhanced to show the injection of nanosensors into skin when mounted as shown in FIG. 2A.

In another aspect, a method is provided for injecting nanoparticles into skin (e.g., tattoed) using a transdermal patch including an array of hollow microfabricated micro-needles. Nanosensors as a hydrogel slurry can be micro-injected into skin (e.g., tattooed) and leave no visible mark. Hydrogels and other carriers can fix the nanosensors into the injection site so that instilial fluid flow would not dislodge the nanosensors. As defined herein, a "hydrogel" is a three-dimensional, semi-solid network of one or more polymers derived from in which a relatively large amount of water is present in the wet state. The nanosensor tattoo generally lasts about one week. After a week, the superficial layers of a human's skin are generally sloughed off along with the nanosensor tattoo. Re-application of the nanosensor tattoo may be required using a fresh sensor. FIG. 3 illustrates the formation of a tattoo whereby nanosensors 325 in a hydrogel slurry 335 is injected via the hollow micro-needles array 320 in a spatially-controlled manner into the epidermis, intradermis, or dermis. Thereafter, the substrate can be removed, leaving behind the skin tattoo.

In one embodiment, the carrier is biocompatible, biodegradable or both. Representative, but not limiting, examples of carriers include an FDA-approved, biodegradable dermal fillers such as hyaluronic acid and collagen; biocompatible/biodegradeable hydrogel that is a thermoresponsive polymer that can form a rigid gel at body temperature at the injection site and act as a mechanical fixation agent for the nanosensors; materials such as poly(N-isopropylacrylamide) are injectable, free-flowing viscous solutions at room temperature and rigid gels at body temperature; alginate can be used as an injectable hydrogel that gels in situ in the presence of calcium ions; and thiolated polymers can be used in conjunction with diacrylate crosslinkers that would undergo a Michael addition reaction and gel in situ. Such viscous hydrogels could be modulated with respect to their stiffness by increasing the crosslinking concentration. Overall, the resulting hydrogels can provide mechanical rigidness to prevent the interstitial fluid from washing away the nanosensors from the site of injection.

In another embodiment, nanosensors having a specific shape are provided for fixing nanoparticles into the injection site. The nanosensors can be fabricated to have high aspect ratio shapes such as rods and elipses so that they may be less likely to be dislodged in the skin from interstitial fluid flow. The film stretching technique can be used to fabricate nanosensors in the shape of high aspect ratio rods.

In another embodiment, the polymer matrix embedding or encapsulating the nanosensors can manipulated into a form, e.g., electrospun PCL nanofibers, to aid in intradermal fixation.

Nanosensors which target different molecules and are excited by different wavelengths of light can be used in the same sensor or tattoo to allow for detection of multiple analytes. Thus, in certain aspects, the disclosure provides an epidermal or subdermal injection or tattoo comprising one or more analyte-sensitive nanosensors. In one embodiment, two or more types of nanosensors can be used, each having a different emission wavelength. In still another embodiment, each type of nanosensor has a different excitation and emission wavelength. By designing the nanosensors with this feature, the real time measurement of different target molecules/ions can be obtained with one substrate. That is, using different excitation wavelengths of light, the concentration of different target molecules/ions can be quantified at different times or at approximately the same time. As an added advantage, this allows charting of different measured values at the same time and at a cost savings.

Figure 4:
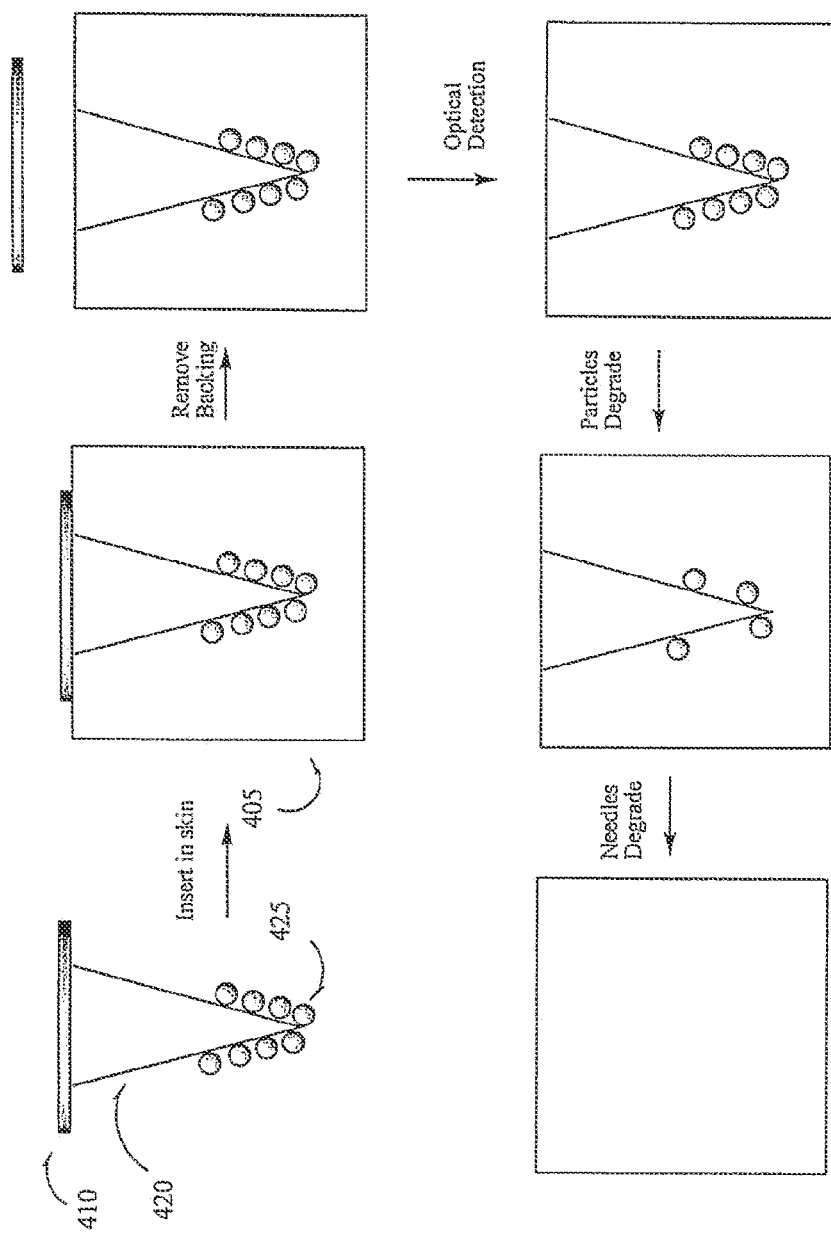
FIG. 4 is a side cross-section of a view enhanced to show the assay component of an example skin-mountable device when mounted as shown in FIG. 2A.

In another embodiment, the micro-needles and the nanosensors can be comprised of a biodegradable material, e.g., PLGA, that degrades at a slower rate relative to the nanosensors. The interface between the micro-needles and the adhesive backing can be comprised of a water-soluble material (PVA or PAA) such that after the micro-needles patch has been applied, water can then be applied to dissolve the water-soluble adhesive material so that the patch can be removed, leaving the micro-needles in the skin. Representative examples of water-soluble adhesive include, PVac adhesives, polyvinayl alcohol, cellulose ethers, methyl cellulose, carboxymethylcellulose, polyvinylpyrrolidone, dextrins, starches, casein, soybean, milk albumin, skin (e.g., animal hides) adhesives, and fish adhesives FIG. 4 illustrates a micro-needle(s) bound to an water soluble adhesive layer between the micro-needle(s) and the substrate 410. Following the application of the skin patch into skin 405, water is applied and the adhesive layer dissolves, releasing the substrate 410 from the micro-needle(s) array 420. After one or measurements of targets are made, both the nanosensors and micro-needles degrade and are absorbed by the body. The nanosensors and micro-needles can have any suitable degradation rate. Typically, the nanosensors and micro-needles can degrade in one or two weeks, depending the selection of polymers used in manufacture.

V. Example Optical Sensor

As shown in the cross-sectional views 200, 202 and 204 in FIGS. 2A, 2B and 2C, the substrate 210 can be mounted on the skin 205 with an inward-facing surface 232 and an outward-facing surface 234. It is noted that relative dimensions in FIG. 2A are not necessarily to scale, but have been rendered for purposes of explanation only in describing the arrangement of the example skin-mountable substrate 210. The substrate 210 can have an optode nanosensor as assay component 230 configured to undergo an optically-detectable change upon interaction with an analyte. In some examples, the optically-detectable change may involve a change in optical absorption, reflectivity, and/or fluorescence. At least a portion of assay component 230 may be embedded in a polymeric material.

As shown in FIG. 2B, the assay component 230 may extend from the inward-facing surface 232 such that the assay component 230 is in direct contact with the skin 205 and penetrates into the intradermis 215 of the skin so as to contact interstitial fluid. In this way, the assay component 230 can interact with an analyte in the interstitial fluid of the skin 205. In some embodiments, the substrate 210 can include a micro-needle array 220, which includes optode nanosensors 225 coating the external surface of the micro-needles, protruding into the intradermis 215 of the skin 205 to enable the assay component 230 to interact with an analyte in the interstitial fluid 270 of the skin 205. In other embodiments, as shown in FIG. 2D, the nanosensors 225 are coating the inner surface 221 of a presentative hollow micro-needle(s) 222, protruding into the intradermis 215 of the skin. In further embodiments, as shown in FIG. 2D, the substrate 210 can include a micro-needle array 220, which includes optode nanosensors 225 encapsulated in a polymeric micro-needle array 226, protruding into the intradermis 215 of the skin 205 to enable the assay component 230 to interact with an analyte in the interstitial fluid 270 of the skin 205.

Assay component 230 can be selectively sensitive to an analyte by including a catalytic reagent such as an enzyme, specific binding agents such haptens, antibodies, or aptamers, and other reagents that selectively interacts with the analyte. A sensitizing layer or coating can be located proximal to the nanosensor 225 of assay component 230. The sensitizing layer can include elements other than elements that selectively interact with the analyte; for example, the sensitizing layer could include a polymer that is permeable to the analyte. An analyte-selective element of the sensitizing layer could be encapsulated in, adsorbed onto, covalently bonded to, or otherwise disposed on or within such a polymer.

In some examples, the sensitizing layer can include one or more ionophores that selectively interact with an ion. In some examples, the ion is potassium, and the ionophore includes one or more of valinomycin, bis[(benzo-15-crown-4)-4'-ylmethyl]pimelate), 2-dodecyl-2-methyl-1,3-propanediyl-bis-[N-(5'-nitro(benzo-15-crown-5)-4'-yl)carbamate], and 4-tert-butyl-2,2,14,14-tetrahomo-4a,14a-dioxacalix[4]arene-tetraacetic acid tetra-tert-butyl ester. Potassium from the interstitial fluid can diffuse on or through the micro-needles 225 and reversibly bind to the ionophore, resulting in an optical change that can be measured by a photodetector.

A protective layer which is permeable to the analyte can be disposed on the sensitizing layer. The protective layer can be composed of a polymer that is permeable to the analyte. The polymer may be formulated to include porogens to tailor the permeability to the analyte of the protective layer for a specific application. In some examples, the sensitizing layer could be selectively sensitive to one or more analytes in addition to the analyte of interest. In those examples, the protective layer could be configured to be impermeable to the one or more analytes, such that only the analyte of interest was able to both diffuse through the protective layer and interact with the sensitizing layer.

The assay component 230 can include components that allow for the optical detection of a select analyte by a reader. For example, the assay component may include assay components that undergo a detectable change, e.g., in optical absorption, reflectivity or fluorescence, upon interaction with an analyte. In such embodiments, the reader may be placed over the substrate and measure the analyte by detecting the change in optical property. The reader device may include a excitation light source configured to direct light toward the substrate, and a photodetector configured to detect light emission from the substrate.

The system may further include one or more data collection systems for interrogating, in a non-invasive manner, the nanosensor. In one example, the system includes a detector configured to detect a response signal transmitted from the sensor. The response signal can include both an analyte response signal, which can be related to the interaction of the one or more target analytes with the nanosensor, and a background noise signal. For example, the nanosensor may include a fluorescent labels configured to produce a fluorescence signal in response to a chemical reaction initiated, at least in part, to the presence of the target analyte.

In some examples, the system may include an interrogating signal source for transmitting an interrogating signal in the form of an excitation light that can penetrate into the sensor following exposure to the analyte and a detector for detecting a response signal that is transmitted from the sensor, in response to the interrogating signal. The interrogating signal can be any kind of optical signal that results in a response signal that can be used to measure a physiological parameter or, more particularly, that can detect the binding or interaction of the clinically-relevant analyte to the sensor. In one example, where the sensor includes fluorescence nanosensors, the interrogating signal is an optical signal with a wavelength that can excite the fluorophore in the sensor (e.g., a wavelength in the range of about 500 to about 1000 nanometers), and the response signal is fluorescence radiation from the fluorophore that can reach the detector.

In some cases, an interrogating signal is not necessary to measure one or more of the physiological parameters and, therefore, the wearable device 100 may not include a signal source 170. For example, the nanosensors can include an autofluorescent or luminescent marker, such as a fluorophore, that will automatically emit a response signal indicative of the binding of the clinically-relevant analyte to the nanosensors, without the need for an interrogating signal or other external stimulus. In some examples, the nanosensors may include a chemiluminescent marker configured to produce a response signal in the form of luminescence radiation produced in response to a chemical reaction initiated, at least in part, to the binding of the target analyte to the particle.

Additionally, the system may further include a modulation source configured to modulate the analyte response signal. The modulation source can be configured to modulate the analyte response signal differently than the background noise signal. To this end, the modulation may help to discern between the target analyte and, essentially, everything else in the body by, for example, increasing the signal-to-noise ratio. Generally, the modulation may include any spatial, temporal, spectral, thermal, magnetic, mechanical, electrical, acoustic, chemical, or electrochemical, etc. modulation technique or any combination thereof.

In some scenarios, it may also be useful to detect and distinguish both the analyte response signal—related to nanosensor bound to or interacting with target analyte(s)— and an "unbound" nanosensor signal—related to nanosensors bound to or interacting with target analyte(s). For example, in some measurement or characterization schemes, it may be useful to determine the percentage of nanosensors present in the sensor that have bound to the target analyte. In such cases, the modulation source may be configured to modulate the analyte response signal differently than the unbound nanosensor signal.

The elements of the system, namely the type of modulation, the types of nanosensors and target analytes may all be interrelated. Ultimately, the type of nanosensors used to detect a particular target analyte may depend, to some extent, on the characteristics of the target analyte (i.e., type, size, shape, affinities, etc.) and the chosen type of modulation (i.e., spatial, spectral, thermal, magnetic, mechanical, chemical, etc.).

V. Example Substrate/Reader Interactions

FIG. 5A is a diagram of an example system 500. The substrate 510 is mounted on a surface of skin 505 (i.e., a skin-mounted substrate) and an external reader 580 is positioned proximate to the substrate 410. It is noted that relative dimensions in FIG. 5A are not necessarily to scale, but have been rendered for purposes of explanation.

In one embodiment, the substrate 510 may include optode nanosensors as an assay component 540. FIG. 5B is a block diagram of a system described in connection with substrate 510 and reader 580 in FIG. 5A. System 504 includes a substrate 510 operated by a reader 580 to obtain one or more measurements related to an analyte in interstitial fluid of the skin. An assay component 540 configured to undergo an optically-detectable change 526 related to the analyte can be included with substrate 510. The optically-detectable change 526 may include a change in at least one of optical absorption, reflectivity, or fluorescence. As shown in FIG. 5A, substrate 510 is configured to be contact-mounted over an external skin surface 505.

The skin-mounted assay component 540 can be operated to a light source from the reader 580. The reader 580 may include a light source 516 configured to direct light 524 toward the assay component 540 of the substrate 510, and a photodetector 518 configured to detect light 526 from the assay component 540. For example, the substrate 510 may include nanosensors as an assay component 540 that fluoresces upon interaction with an analyte. The reader 580 may be placed proximate to the substrate 510 so that the light source 516 may provide light 524 to the assay component 540. If the analyte is present, the assay component 540 may fluoresce, and the fluorescence 526 may be detected by the photo detector 518.

In other embodiments, sensor 530 can further include and/or be replaced by sensor(s) that measure light, heat/temperature (e.g., body temperature), blood pressure, air flow, altitude, and/or other characteristics than analyte concentration(s). In these other embodiments, sensor 530 can communicate data about the measured characteristics to reader 480 using backscatter communication 522.

VI. Example Readers

The system includes a reader device ("reader") that is configured to detect the interaction between the substrate and the analyte in the interstitial fluid. The reader can be a smart phone, digital assistant, or other portable computing device with wireless connectivity sufficient to communicate with the substrate. The function of the reader can be included in a "wearable device." The term "wearable device," as used in this disclosure, refers to any device that is capable of being worn at, on or in proximity to a body surface, such as a wrist, ankle, waist, chest, or other body part, e.g., an eye-glass frame, a head-mountable computer frame, a cap, a hat, part of a hat or cap (e.g., a hat band or bill of a baseball cap), a headphone headband, a watch, etc. In some examples, the reader is positioned proximate to the substrate only when a measurement is desired. In other examples, the reader is mounted proximate to the substrate so that the analyte-substrate interaction can be detected on demand or continuously without having to position the reader.

Figure 6A:
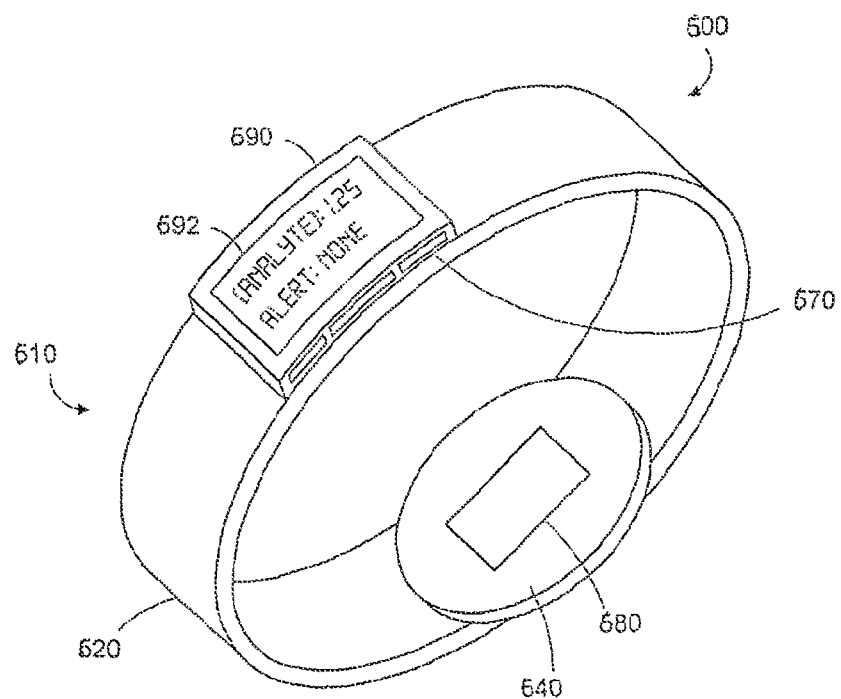
FIG. 6A is an example reader included in a wearable device in accordance with an example embodiment
Figure 6B:
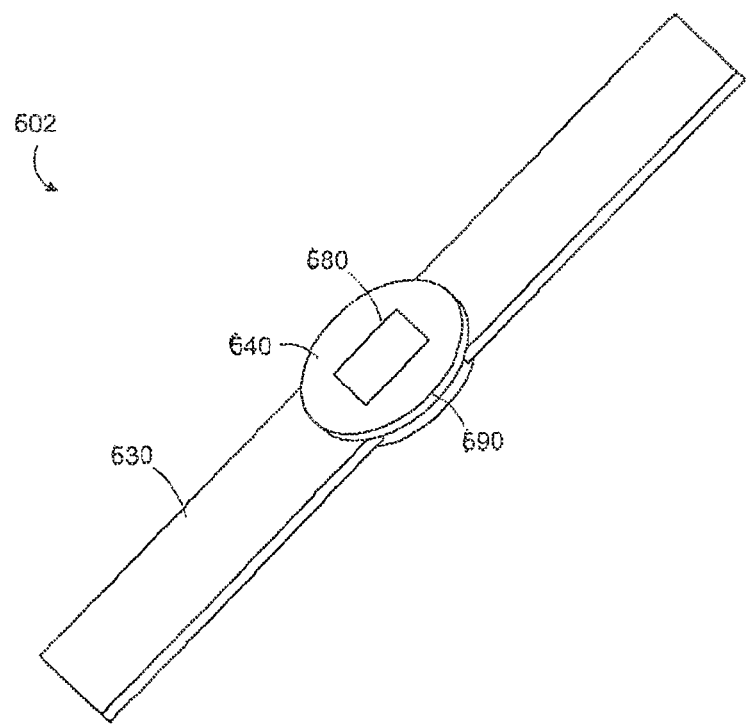
FIG. 6B is an example reader included in a wearable device in accordance with an example embodiment

FIGS. 6A and 6B show example wearable devices 600 and 602. The device may be placed in close proximity to the substrate, but need not be touching or in intimate contact therewith. A mount 610, such as a belt, wristband, ankle band, etc. can be provided to mount the device at, on or in proximity to the body surface. The mount 610 may prevent the wearable device from moving relative to the body to reduce measurement error and noise. In some embodiments, the wearable device is placed directly over the substrate. In one example, shown in FIG. 6A, the mount 610, may take the form of a strap or band 620 that can be worn around a part of the body. Further, the mount 610 may be an adhesive substrate for adhering the wearable device 600 to the body of a wearer.

A reader platform 640 is disposed on the mount 610 such that the reader platform 540 can be positioned proximate to the substrate. The reader platform 640 may house the reader components 680 shown in FIG. 1. The wearable device 600 may also include a user interface 690 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 690 may include a display 692 where a visual indication of the alert or recommendation may be displayed. The display 692 may further be configured to provide an indication of the measured physiological parameters, for instance, the concentration of a measured analyte.

In another embodiment, as shown in FIG. 6B, the reader platform 640 may be positioned on the back side of the user interface 690.

In some embodiments, a reader can power a sensor in the substrate using a low-power transmission; e.g., a transmission of 1 watt or less of power. In these embodiments, the reader can be within a predetermined distance; e.g., 1 foot, 40 cm, of the substrate.

After receiving analyte-related data from the substrate, the reader can utilize the data; e.g., process, present, store, communicate, etc. For example, the reader can process the analyte-related data to generate an analyte concentration, and the display device can present the analyte concentration to the user.

In some embodiments, the reader may evaluate the analyte-related data and display a visual indication of an alert or recommendation and/or an indication of the measured physiological parameters. For example, the reader may compare an analyte concentration to a low- and/or high-analyte threshold(s) to determine, respectively, whether the analyte concentration is too high or low for the wearer of the system. If the blood-glucose data is too high or low for wearer, the display can alert wearer, attempt to contact another person or entity to help the wearer, and/or perform some other action.

Further, the user interface 690 may include one or more buttons 670 for accepting inputs from the wearer. For example, as shown in FIG. 6A, the buttons 670 for accepting inputs from the wearer. The buttons 670 may be configured to change the text or other information visible on the display 692. The buttons 670 may also be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

VII. Example Operations

In some embodiments, the present disclosure provides a method for operating a system including a substrate and a reader to measure an analyte concentration of a fluid in the skin.

Figure 7:
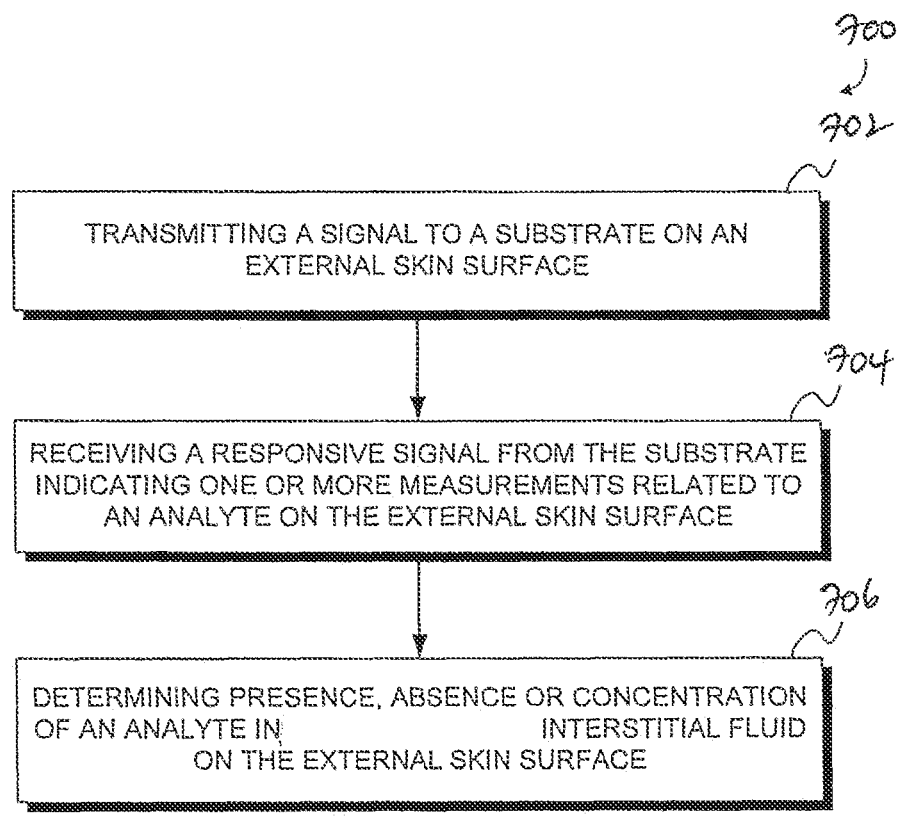
FIG. 7 is a flowchart of an example method for operating a system with an external reader and a skin-mounted substrate to measure an analyte in a fluid in the skin.

FIG. 7 is a flowchart of a method 700 for operating a system including a reader and a substrate mounted to an external skin surface to measure an analyte in interstitial fluid in the skin. The method includes transmitting a signal to a substrate on an external skin surface (702). In some examples, the substrate includes an antenna and the signal is a radio frequency (RF) signal. In other embodiments, the signal may be optical, such as visible light or fluorescent light. The method further includes receiving a responsive signal from the substrate (704). The responsive signal may indicate one or more measurements related to an analyte on the external skin surface. For example, when the substrate includes an antenna, the responsive signal may be a radio frequency (RF) signal. In other examples, the responsive signal may be an optical signal, such as a change in optical absorption, reflectivity, or fluorescence. In some embodiments, the method may further include determining the presence, absence or concentration of an analyte in the interstitial fluid on the external skin surface (706). In embodiments where the substrate includes an electrochemical sensor selectively sensitive to an analyte, the concentration of the analyte may be determined. In embodiments where the substrate includes a component configured to undergo an optically-detectable change related to an analyte, the presence, absence or concentration of the analyte, may be determined.

VIII. Conclusion

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The example embodiments described herein and in the figures are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The invention claimed is:

1. A device comprising:
   a plurality of micro-needles, each having a base end and a tip;
   a planar optically transparent substrate directly attached to the base ends of the micro-needles, wherein the substrate can attach to an external skin surface such that the micro-needles penetrate into the skin;
   nanoparticles associated with the micro-needles, the nanoparticles having an optically detectable label for interacting with a target analyte present in interstitial fluid; and
   water-soluble adhesive material for attaching the base ends of the micro-needles to the substrate.

2. The device of claim 1, wherein the adhesive material is located on the substrate for attaching the substrate to the external skin surface and for attaching the base ends of the micro-needles to the substrate.

3. The device of claim 2, wherein the adhesive is water-soluble such that the substrate can be detached from the base end of the micro-needles and from the external skin surface in the presence of water.

4. The device of claim 1, wherein the micro-needles are arranged in a three dimensional spatially-controlled array.

5. The device of claim 1, wherein the micro-needles are solid, hollow or porous.

6. The device of claim 1, wherein the nanoparticles are bound to a surface of the micro-needles.

7. The device of claim 1, wherein the nanoparticles are encapsulated in the micro-needles.

8. The device of claim 1, wherein the micro-needles comprise hollow or porous spaces comprising the nanoparticles.

9. The device of claim 1, wherein the micro-needles, the nanoparticles, or both are biodegradable.

10. The device of claim 1, wherein the micro-needles are non-dissolvable and are coated with a dissolvable coating of a polymer and the nanoparticles.

11. A system comprising:
   (a) a skin-mountable device, comprising:
      a plurality of micro-needles, each having a base end and a tip;
      a planar optically transparent substrate directly attached to the base ends of the micro-needles, wherein the substrate can attach to an external skin surface such that the micro-needles penetrate into the skin; and nanoparticles associated with the micro-needles, the nanoparticles having an optically detectable label for interacting with a specific target analyte present in interstitial fluid;

water-soluble adhesive material for attaching the base ends of the micro-needles to the substrate; and (b) a reader device, wherein the target analyte can be detected by the reader device via interaction with the skin-mountable device.

12. The system of claim 11, wherein the detectable label comprises a fluorophore.

13. The system of claim 12, wherein the target analyte can be detected by the reader device by optically interrogating the nanoparticles in the skin-mountable device.

14. The system of claim 13, wherein the reader device comprises:
a light source; and
a photodetector, wherein light is directed toward the substrate by the light source and wherein light from the substrate is detected by the photodetector.

15. The system of claim 14, wherein an optically-detectable change related to the nanoparticles interacting with the target analyte is detected by the reader device.

16. The system of claim 15, wherein the optically-detectable change comprises a change in at least one of optical absorption, reflectivity, or fluorescence.

17. The system of claim 16, wherein the optically-detectable change is fluorescence.

18. The system of claim 11, wherein the skin-mountable device further comprises an antenna, and wherein the target analyte is detected by the reader device based on data communicated via the antenna.

19. The system of claim 18, wherein the data communicated via the antenna is indicative of one or more measurements obtained by the skin-mountable device.

20. The system of claim 11, wherein the reader device is a wearable device.

21. A method, comprising:
mounting a skin-mountable device to a skin surface, wherein the skin-mountable device comprises (i) a plurality of micro-needles, each having a base end and a tip, (ii) a planar optically transparent substrate directly attached to the base ends of the micro-needles, wherein the substrate can attach to an external skin surface such that the micro-needles penetrate into the skin, (iii) nanoparticles associated with the micro-needles, the nanoparticles having a fluorophore for interacting with a target analyte present in interstitial fluid, and (iv) water-soluble adhesive material for attaching the base ends of the micro-needles to the substrate;

transmitting incident light from a reader device to the skin-mountable device;

receiving, by the reader device, fluorescence light emitted by the nanoparticles interacting with the target analyte in response to the incident light;

detecting the target analyte based on the fluorescence light received by the reader; and removing the planar optically transparent substrate from the skin surface and from the micro-needles.

22. The method of claim 21, wherein detecting the target analyte based on the fluorescence light received by the reader comprises determining a concentration of the target analyte in the interstitial fluid based on the fluorescence light received by the reader.

23. The method of claim 21, wherein the substrate comprises a polymeric material transparent to the incident light and the fluorescence light.

24. The method of claim 21, wherein the target analyte is $Na^+$, $K^+$, $Ca^{2+}$, glucose, urea, creatinine, bicarbonate, or chloride.

* * * * *